US00PP10424P

United States Patent [19]

Bolwijn

[11] Patent Number: Plant 10,424

[45] Date of Patent: Jun. 2, 1998

[54] EUONYMUS PLANT NAMED 'INTERBOLWI'

[75] Inventor: Gustaaf Emiel Ferdinand Bolwijn, Putten, Netherlands

[73] Assignee: Spring Meadow Nursery, Inc., Grand Haven, Mich.

[21] Appl. No.: 802,396

[22] Filed: Feb. 18, 1997

[51] Int. Cl.[6] ..... A01H 5/00

[52] U.S. Cl. ..... Plt./63

[58] Field of Search ..... Plt./63

[56] References Cited

U.S. PATENT DOCUMENTS

P.P. 4,340 12/1978 Nielsen ..... Plt./63
P.P. 6,127 3/1988 Dugan ..... Plt./63

*Primary Examiner*—James R. Feyrer
*Attorney, Agent, or Firm*—C. A. Whealy

[57] ABSTRACT

A distinct cultivar of Euonymus plant named 'Interbolwi', characterized by its showy green and yellow variegated foliage; compact, spreading and rounded plant form; moderate growth rate; flat leaves; and excellent resistance to leaf spot diseases. It is intended that the new Euonymus will be marketed under the trade name Blondy.

2 Drawing Sheets

The present invention relates to a new and distinct cultivar of Euonymus plant, botanically known as *Euonymus fontunei*, and hereinafter referred to by the cultivar name Interbolwi. It is intended that the new Euonymus will be marketed under the trade name Blondy.

The new cultivar is a naturally-occurring leaf color mutation of the *Euonymus fortunei* cultivar Sunspot (disclosed in U.S. Plant Pat. No. 4,340). In 1988, the new cultivar was discovered by the inventor in a controlled environment in Putten, The Netherlands, within a population of plants of the cultivar Sunspot.

Asexual reproduction of the new cultivar by hardwood or softwood cuttings taken at Putten, The Netherlands, has shown that the unique features of this new Euonymus plant are stable and reproduced true to type in successive generations of asexual reproduction.

The following traits have been repeatedly observed and are determined to be the unique characteristics of 'Interbolwi'. These characteristics in combination distinguish 'Interbolwi' as a new and distinct cultivar:

1. Showy green and yellow variegated foliage.
2. Compact, spreading and rounded plant form.
3. Moderate growth rate.
4. Flat leaves.
5. Excellent resistance to leaf spot diseases.

In side-by-side comparisons in Grand Haven, Mich., under commercial practice, plants of the new Euonymus differed from plants of the parent cultivar Sunspot in the following characteristics:

1. Plants of the new Euonymus are more compact than plants of the cultivar Sunspot.
2. Plants of the new Euonymus are more spreading than plants of the cultivar Sunspot.
3. Stems of plants of the new Euonymus have more green streaking than stems of plants of the cultivar Sunspot.
4. Upper foliage surfaces of plants of the new Euonymus have a dull appearance whereas upper foliage surfaces of plants of the cultivar Sunspot are glossy.
5. Leaves of the new Euonymus are flatter than leaves of the cultivar Sunspot.
6. Foliage variegation is more pronounced on plants of the new Euonymus compared to plants of the cultivar Sunspot. Plants of the new Euonymus are considered more showy than plants of the cultivar Sunspot.
7. Foliage variegation color on plants of the new Euonymus is more golden than foliage variegation color on plants of the cultivar Sunspot.

8. Plants of the new Euonymus are more resistant to leaf spot diseases than plants of the cultivar Sunspot.

Plants of the new Euonymus can be compared to plants of the cultivar Moonshadow (disclosed in U.S. Plant Pat. No. 6,127), an Euonymus cultivar that is also a naturally-occurring mutation of the cultivar Sunspot. In side-by side comparisons in Grand Haven, Mich., under commercial practice, plants of the new Euonymus differed from plants of the cultivar Moonshadow in the following characteristics:

1. Plants of the new Euonymus are more compact than plants of the cultivar Moonshadow.
2. Plants of the new Euonymus are more vigorous than plants of the cultivar Moonshadow.
3. Stems of plants of the new Euonymus have more green streaking than stems of plants of the cultivar Moonshadow.
4. Upper foliage surfaces of plants of the new Euonymus have a dull appearance whereas upper foliage surfaces of plants of the cultivar Moonshadow are glossy.
5. Leaves of the new Euonymus are flatter and wider than plants of the cultivar Moonshadow.
6. Foliage variegation is more pronounced on plants of the new Euonymus compared to plants of the cultivar Moonshadow. Plants of the new Euonymus are considered more showy than plants of the cultivar Moonshadow.
7. Foliage variegation color on plants of the new Euonymus is more golden than foliage variegation color on plants of the cultivar Moonshadow.
8. Plants of the new Euonymus are more resistant to leaf spot diseases than plants of the cultivar Moonshadow.

The cultivar Interbolwi has not been observed under all possible environmental conditions. The phenotype may vary somewhat with variations in environment such as temperature and light intensity, without, however, any variance in genotype.

The following observations, measurements and comparisons describe plants grown in Grand Haven, Mich., in a double polyethylene-covered greenhouse with day temperatures ranging from 5 to 26.5C and night temperatures ranging from 5 to 15.5C.

The accompanying colored photographs illustrate the overall appearance of the new Euonymus, showing the colors as true as it is reasonably possible to obtain in colored reproductions of this type.

The first photograph comprises a top perspective view of typical plants of the cultivar Interbolwi.

The second photograph comprises a close-up view of individual stems of the cultivar Interbolwi showing the green and yellow variegation pattern. Foliage colors in the photographs may appear different than the actual colors due to light reflectance.

In the following description, color references are made to The Royal Horticultural Society Colour Chart except where general terms of ordinary dictionary significance are used.

*Botanical classification: Euonymus fortunei* cultivar Interbolwi.

*Parentage:* Naturally-occurring leaf color mutation of *Euonymus fortunei* cultivar Sunspot (U.S. Plant Pat. No. 4,340).

Propagation:

*Type cutting.*—Hardwood or softwood cuttings.

*Time to initiate and develop roots.*—Summer: About 21 days at 22C. Winter: About 40 days at 120C.

*Rooting habit.*—Fleshy and well-branched. Grey-brown aerial roots are occasionally observed.

Plant description:

*Form.*—Compact, rounded, spreading perennial plant.

*Branching habit.*—Basally branching, pruning increases branching.

*Plant height.*—38 to 50 cm from soil level to top of plant plane.

*Plant diameter or area of spread.*—60 to 90 cm.

*Vigor.*—Moderate.

*Stem description.*—Lateral branch diameter: About 2 mm. Internode length: 1.5 to 2.5 cm. Color: 14C/14D with green, 143C, streaks. Texture: Glabrous.

*Foliage description.*—Leaves single and generally symmetrical, opposite arrangement. Usually 10 to 20 leaves per lateral branch. Size (largest leaves): Length: 2 to 4 cm. Width: 1 to 2.2 cm. Shape: Ovate to elliptic. Apex: Obtuse. Base: Cuneate. Margin: Crenate/serrate. Texture: Smooth and leathery with a dull finish. Aspect: Flat. Color: Variegated with yellow and green patterns that are variable. Usually at least 60% of the leaf surface area is yellow. Young and fully expanded leaves: Upper surface: Center: 14C/14D. Margin: 147A. Upper surface: Center: 14D Margin: 147A. Petiole: Length: 3 to 5 mm. Diameter: 1 mm or less. Color: 14C/14D.

Flower description: Flowers have not been observed on plants of the new Euonymus grown to date.

Disease resistance: Plants of the new Euonymus have shown excellent resistance to leaf spot diseases.

It is claimed:

1. A new and distinct cultivar of Euonymus plant named 'Interbolwi', as illustrated and described.

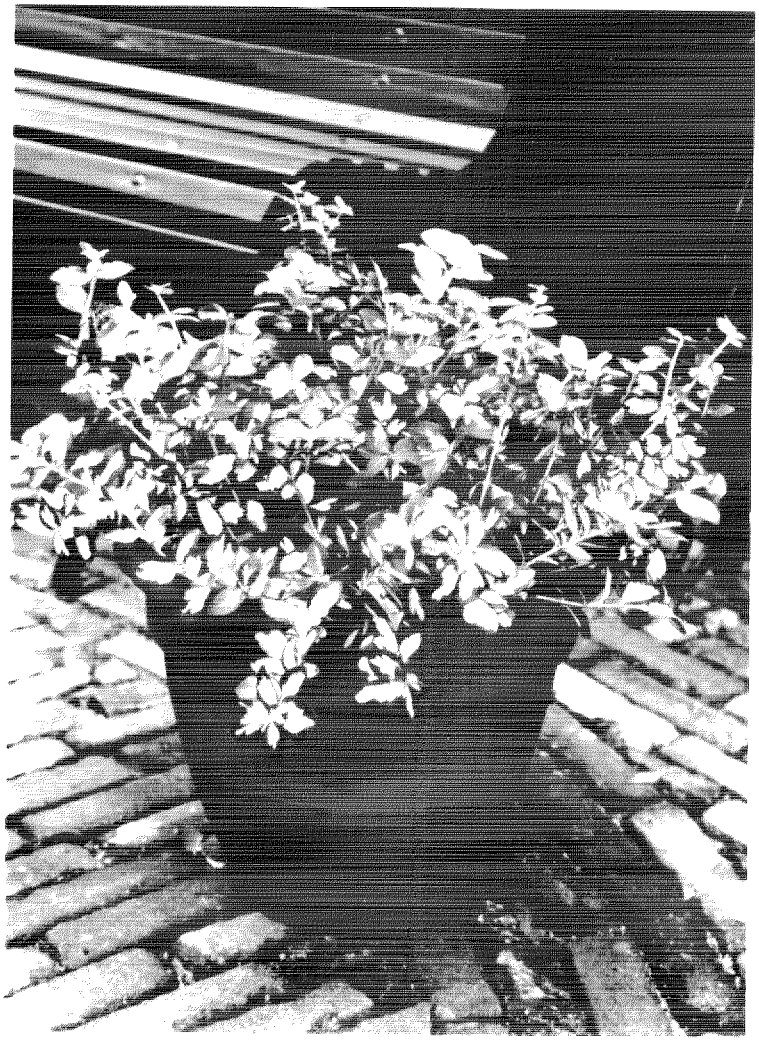

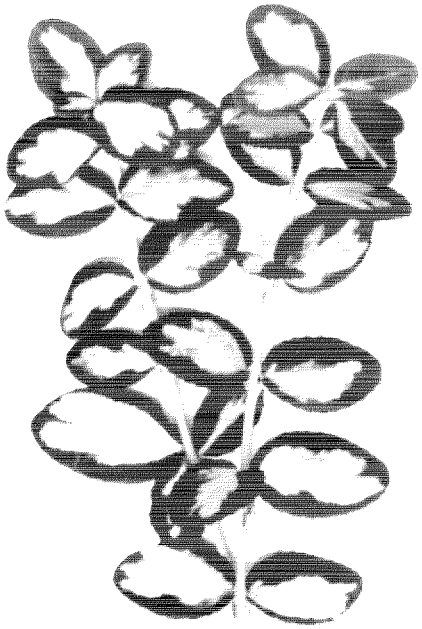

* * * * *